(12) United States Patent
Hoglen

(10) Patent No.: US 6,509,471 B2
(45) Date of Patent: Jan. 21, 2003

(54) 3-SUBSTITUTED PYRIDINE COMPOUNDS AND RELATED SYNTHESIS

(75) Inventor: Dean Kent Hoglen, Baton Rouge, LA (US)

(73) Assignee: Syngenta Participations AG (CH)

(*) Notice: Subject to any disclaimer, the term of this patent is extended or adjusted under 35 U.S.C. 154(b) by 0 days.

(21) Appl. No.: 09/767,269

(22) Filed: Jan. 22, 2001

(65) Prior Publication Data

US 2001/0006805 A1 Jul. 5, 2001

Related U.S. Application Data

(63) Continuation of application No. PCT/EP99/05130, filed on Jul. 7, 1999.
(60) Provisional application No. 60/172,230, filed on Jul. 21, 1998.

(51) Int. Cl.$^7$ ............... C07D 213/65; C07D 213/70
(52) U.S. Cl. ............... 546/303; 546/296
(58) Field of Search ............... 546/296, 303

(56) References Cited

U.S. PATENT DOCUMENTS

| | | | |
|---|---|---|---|
| 3,828,056 A | 8/1974 | Kreider | 546/274.7 |
| 4,435,206 A | 3/1984 | Levitt | 544/212 |
| 4,522,645 A | 6/1985 | Levitt | 544/209 |
| 4,579,583 A | 4/1986 | Fory et al. | 544/122 |
| 4,756,739 A | 7/1988 | Fuss et al. | 546/24 |
| 5,369,083 A | * 11/1994 | Schurter et al. | 504/215 |
| 5,403,814 A | 4/1995 | Fory | 504/215 |
| 5,721,364 A | 2/1998 | Hoglen et al. | 544/219 |
| 6,069,144 A | 5/2000 | Wagner et al. | 514/252 |

FOREIGN PATENT DOCUMENTS

| | | |
|---|---|---|
| EP | 0 582 021 A | 2/1994 |
| JP | 08 245590 A | 9/1996 |

OTHER PUBLICATIONS

Chen, Ping et al.: "Amino Diol HIV Protease Inhibitors. Synthesis and Structure–Activity Relationships of P1/P1' Compounds: Correlation between Lipophilicity and Cytotoxicity", J. Med. Chem. (1996) 39(10), 1991–2007 XP002122710 3–(2–bromoethoxy)pyridine on p. 2001.

Fuss, Andreas et al: "Chemistry of 3–hydroxypyridine. Part 3. Synthesis of substituted 3–'fluoro(chloro)alkoxy?pyridines from halo– or amino–3–hydroxypyridines" Synthesis (1990), (7), 604–608. XP002122711 Scheme A.

March et al., "Advanced Organic Chemistry," 4th Edition, John Wiley & Sons (1992), pp. 721–725.

Giam et al., J. Chem. Soc., Chem. Commun., 1980, pp. 756–757.

Kikukawa et al., J. Org. Chem., 1981, vol. 46, pp. 4885–4888.

Roe et al., J. Amer. Chem. Soc., 1952, vol. 74, pp. 6297–6298.

Schickh et al., Berichte d. D. Chem. Gesellschaft, 1936, vol. 69, pp. 2593–2605.

Heterocyclic Compounds, vol. 14, supplement part 3, p. 74 (1974).

R.N. Butler, Chemical Reviews, 1975, vol. 75, No. 2, p. 250.

Nathan Kornblum, Organic Reactions, vol. 2, p. 262 (1944).

Hay, "Chemistry of Sulfonylurea Herbicides," Pestic. Sci. (1990) vol. 29, pp. 247–261.

* cited by examiner

*Primary Examiner*—Bernard Dentz
(74) *Attorney, Agent, or Firm*—William A. Teoli; Thomas Hamilton

(57) ABSTRACT

The present invention relates to 3-substituted and 2,3-disubstituted pyridine compounds which are useful as intermediates in the synthesis of pyridylsulfonylurea herbicides. The invention also relates to arylation of alcohols using a pyridinediazonium salt. More particularly the arylation process of the instant invention relates to the synthesis of 2,3-disubstituted pyridine compounds via anhydrous diazotization of 3-aminopyridines to form a diazonium salt intermediate that is then reacted with the appropriate alcohol to produce the desired product. The invention additionally relates to pyridine-3-diazonium salt intermediates.

12 Claims, No Drawings

3-SUBSTITUTED PYRIDINE COMPOUNDS AND RELATED SYNTHESIS

This application is a continuation of PCT/EP99/05130 filed Jul. 7, 1999, which claims the benefit of provisional application 60/172,230 filed Jul. 21, 1998.

FIELD OF THE INVENTION

The present invention relates to 3-substituted and 2,3-disubstituted pyridine compounds which are useful as intermediates in the synthesis of pyridylsulfonylurea herbicides. The invention also relates to arylation of alcohols using a pyridinediazonium salt. More particularly the arylation process of the instant invention relates to the synthesis of 2,3-disubstituted pyridine compounds via anhydrous diazotization of 3-aminopyridines to form a diazonium salt intermediate that is then reacted with the appropriate alcohol to produce the desired product. The invention additionally relates to pyridine-3-diazonium salt intermediates.

BACKGROUND OF THE INVENTION

Arylation reactions involving dediazotization of a diazonium salt have been used to introduce various groups on to an aryl ring. March et al., *Advanced Organic Chemistry*, 4$^{th}$ Ed., John Wiley & Sons, (1992), pages 721–725. Aromatic and heteroaromatic sulfides have been successfully prepared from primary aromatic and heteroaromatic amines by adding the appropriate amine to a solution of isopentyl nitrite and excess of dimethylsulfide which is heated to 80–90° C. Giam et al., J. Chem. Soc., Chem. Commun., 1980, 756–757. Arylation of olefins by the combination of arylamines (such as 3-aminopyridine) and tert-butyl nitrite under palladium catalysis in the presence of acid has also been described in the chemical journal literature. Kikukawa et al., J. Org. Chem., 1981, Vol.46, 4885–4888. It is believed that the reaction of an arylamine and an alkyl nitrite gives an aryl radical under neutral conditions, whereas it affords a diazonium salt under acidic conditions. Replacement of the primary aromatic amino group by hydrogen has been accomplished by decomposing diazonium fluoborates in the presence of ethanol and zinc, however, when 3-aminopyridine is used, an additional by-product is obtained as the 3-ethoxypyridine in low yield (12.2%). Roe et al., J. Amer. Chem. Soc. 1952, Vol. 74, 6297–6298. 2-chloro-3-hydroxypyridine has been prepared by reacting 3-amino-2-chloropyridine with a nitrite in the presence of acid. Schickh et al., Berichte d. D. Chem. Gesellschaft, 1936, Vol. 69, 2593–2605.

The relative reactivity of aniline derivatives and primary aminopyridine compounds is not analogous in the context of diazotization and de-diazotization reactions. It would be overly simplistic to view the pyridine ring as analogous to a benzene (i.e. pyridine is not a benzene ring merely having a nitrogen ring atom therein). There is a dramatic difference in the reactivity of benzene and pyridine moieties that is caused by the presence and electronic effects of the nitrogen in the ring of the latter. Similarly, there may be significant differences in the stability of the corresponding benzenediazonium salts and pyridinediazonium salts containing these moieties. Additionally, 3-aminopyridine moieties are not functionally equivalent to 2-aminopyridine moieties when considered in the context of diazotization-dediazotization reactions. The electronic effects and chemistry are completely different for the diazonium salts prepared from 2-aminopyridines as compared to the diazonium salts prepared from 3-aminopyridines. The most relevant difference is that pyridine-2-diazonium salts are very unstable and can not be isolated. See *Heterocyclic Compounds*, Volume 14, supplement part 3, page 74 (1974) and R. N. Butler, *Chemical Reviews*, 1975, Volume 75, No. 2, page 250.

What is commonly observed when a diazonium salt is treated with an alcohol is reduction of the diazonium salt ($ArN_2^+$) to the ArH species. For a general discussion of diazonium chemistry see Nathan Kornblum, *Organic Reactions*, Volume 2, page 262 (1944). Surprisingly, it has now been discovered that the use of halogenated alcohols yields the corresponding alkoxide as the major product.

DETAILED DESCRIPTION OF THE INVENTION

One embodiment of the invention is the compounds of formula I:

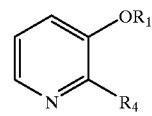

(I)

wherein $R_1$ is a $C_1$–$C_4$ haloalkyl and $R_4$ is H, halogen or $C_1$–$C_4$ alkylthio; and acid addition salts thereof. The haloalkyl groups may be branched or unbranched. The halogen(s) of the haloalkyl group and $R_4$, when halogen, are independently selected from fluoro, chloro, bromo and iodo. The degree of halogen substitution of $R_1$ may range from monohalogen substitution to polyhalogen substitution wherein all the hydrogens of the alkyl group have been replaced by halogens (e.g. perfluoroalkyl groups). Compounds of formula Ia constitute preferred embodiment of the invention:

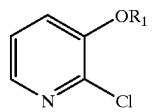

(Ia)

wherein $R_1$ is defined as above. Another preferred embodiment of the invention is wherein $R_1$ is selected from the group consisting of —$CH_2CF_3$, —$CH_2CCl_3$, and —$CH_2CH_2Cl$. An ultimately preferred embodiment of the invention is the compound having the formula:

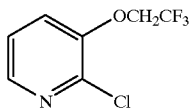

2-chloro-3-(2,2,2-trifluoroethoxy)pyridine.

Another aspect of the invention is the pyridinediazonium salt of formula II:

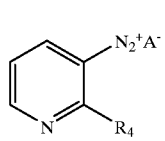

(II)

wherein $A^-$ is a counter-anion derived from an organic acid or inorganic mineral acid, HA; and $R_4$ is defined as above.

A⁻ is preferably an anion of the formula ⁻OSO₂R₂ (i.e. the conjugate base of a sulfonic acid), wherein $R_2$ is $C_1$–$C_4$ alkyl, phenyl, $C_7$–$C_{10}$ alkylaryl, or $C_5$–$C_{10}$ cycloalkyl (preferably methyl); or an anion of the formula ⁻OOC—$R_{2a}$ (i.e. the conjugate base of a carboxylic acid) wherein $R_{2a}$ is $C_1$–$C_4$ haloalkyl, preferably trifluoromethyl; and $R_4$ is defined as above. The pyridinediazonium salt of formula II is useful as an intermediate for the preparation of the compounds of formula I.

A preferred pyridinediazonium salt is the pyridinediazonium sulfonate salt of formula II':

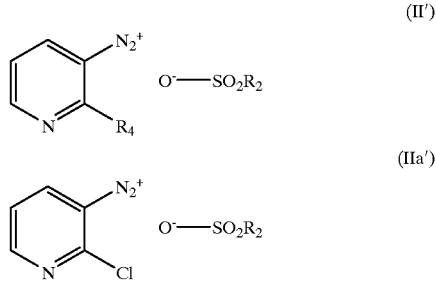

wherein $R_2$ and $R_4$ are defined as above. A preferred feature of the invention is where $R_2$ is methyl or a 10-camphoryl group (i.e. a pyridinediazonium 10-camphorsulfonate salt).

Another aspect of the invention is the product produced from the process of diazotizing a 3-aminopyridine with an alkyl nitrite and acid under substantially anhydrous conditions. The pyridinediazonium salt of formula II or the product from the process of diazotization (to the extent there is a difference) are both features of the instantly disclosed invention. The scope of the invention as to the diazonium salts and the process of preparing the compound of formula I disclosed herein should not be construed to be limited by any particular chemical theory relating to the complexation, equilibration, reaction or acid-base chemistry of the components used to make the diazonium salt or the final product. Another aspect of the invention is pyridinediazonium salts of formula II wherein said salt has interacted chemically so as to result in a changed form of the salt or has interacted with other chemical components so as to form another more stable compound or acid addition salt thereof. Accordingly, the present invention encompasses the substantially unaltered static composition of the appropriate components as well as the chemically integrated composition. "Static composition" denotes 1) the composition composed of components wherein the components have not substantially changed by virtue of their combination or interaction with other composition components, or 2) the composition that has reacted to a point of relative stasis. "Chemically integrated composition" means a composition that results from any equilibration, complexation, dissociation or other chemical transformation (if any) that may occur after combination of the reagents used to prepare the product composition containing the salts of formula II and prior to ultimate use for the preparation of the compounds of formula I. Therefore, the "chemically integrated composition" of the instant invention by definition encompasses the situation where there is an unchanged "static composition" as well as the equilibrated or semi-equilibrated composition existing at any point between initial creation and ultimate use. In other words, the disclosed invention relating to diazonium salts is not limited to a static composition of chemically unaltered constituent components.

The invention also includes the process for obtaining the salts of formula II which are useful as intermediates in the process of preparing the compounds of formula I.

The compounds of formula I are prepared by reacting a salt of formula II under substantially anhydrous conditions with an alcohol having the formula $R_1OH$ wherein $R_1$ is defined above. A preferred process of preparing the compounds of formula I comprises reacting a 3-aminopyridine with an alkyl nitrite in the presence of acid and a solvent/reagent alcohol that reacts with the diazonium salt intermediate generated in situ thereby forming the desired product without isolating the intermediate salt of formula II. See Schemes I and II below.

Scheme I

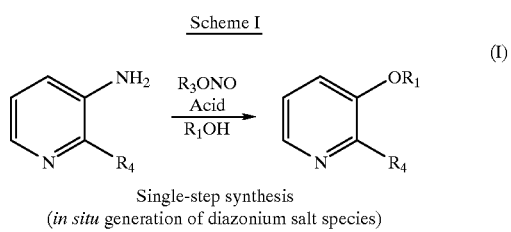

Single-step synthesis
(*in situ* generation of diazonium salt species)

wherein $R_3$ is $C_1$–$C_5$ alkyl, and $R_1$ and $R_4$ are defined as above.

Scheme II

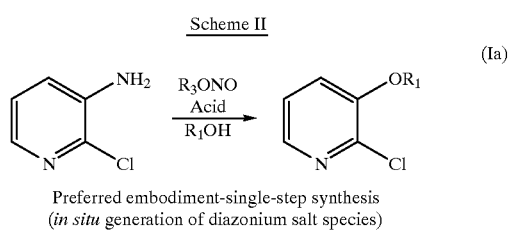

Preferred embodiment-single-step synthesis
(*in situ* generation of diazonium salt species)

The variables in Scheme II are as defined above.

The single-step or "one-pot" procedure depicted in Schemes I and II may be accomplished by adding the alkyl nitrite, preferably t-butyl nitrite, directly to a hot (i.e. 50° C. to 75° C.) solution of the appropriate 3-amino-pyridine and from 0.5 to 2 equivalents of acid, preferably one equivalent of acid, preferably methanesulfonic acid, in the desired alcohol $R_1OH$, preferably 2,2,2-trifluoroethanol thereby generating the desired 3-substituted-pyridine product. An excess amount of the alcohol may be used so that it thereby acts additionally as the solvent in the reaction. Other solvents may be used such as methyl-tertiary-butyl ether (MTBE) or chloroform, either alone or in combination with an alcohol solvent. The solvent or excess alcohol may be removed by distillation, evaporation, under vacuum or otherwise separated from the product using conventional means known in the art.

One of ordinary skill in the art would realize the costs and benefits of preparing the compounds by a "one-pot" or single-step procedure as compared to a two-step procedure wherein the intermediate salt of formula II is heated, transferred to another reaction vessel, purified or otherwise isolated prior to being used in the subsequent dediazotization reaction. Schemes III and IV (below), depict two-step procedures that may be used to make the compounds of formula I and Ia, respectively.

Scheme III:

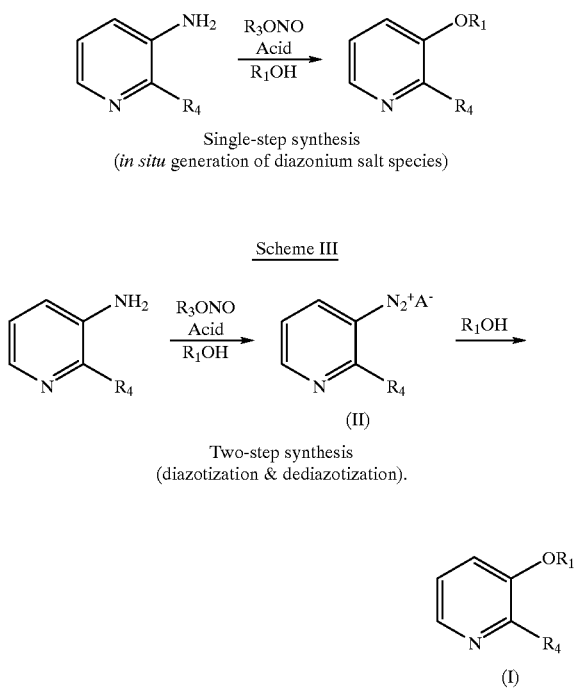

Single-step synthesis
(*in situ* generation of diazonium salt species)

Scheme III

Two-step synthesis
(diazotization & dediazotization).

The variables in the Scheme III are as defined above.

Scheme IV

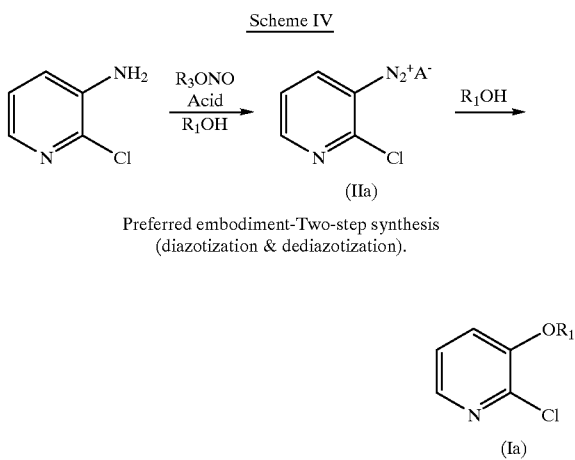

Preferred embodiment-Two-step synthesis
(diazotization & dediazotization).

The variables in the Scheme IV are as defined above.

The two-step procedure depicted in Schemes III and IV may be carried out by dissolving the appropriate 3-aminopyridine in the desired alcohol, $R_1OH$, preferably 2,2,2-trifluoroethanol, in the presence of 0.5 to 2 equivalents acid, preferably one equivalent of acid, preferably methanesulfonic acid. However, other solvents such as MTBE or chloroform may also be used alone or in combination with an alcohol solvent. The alkyl nitrite, preferably t-butyl nitrite, is then added slowly to the 3-aminopyridine solution, preferably at 0° C., thereby generating a diazonium salt. The diazonium salt solution is then either heated followed by addition of the desired alcohol, $R_1OH$ or the solution is added directly without heating to a hot solution of the desired alcohol, $R_1OH$ thereby generating the 3-substituted-pyridine product. The solvent or excess alcohol may be removed by distillation, evaporation, under vacuum or otherwise separated from the product using conventional means known in the art.

The ultimate starting materials, such as 3-amino-2-chloropyridine are either commercially available, may be prepared by known procedures or otherwise may be prepared using conventional chemistry knowledge. Similarly, the alkyl nitrite, acid and alcohol reagents are commercially available, may be prepared by known procedures or may otherwise may be prepared using conventional chemistry knowledge. For example, t-butyl nitrite or isoamyl nitrite are two commercially available nitrites that can be used in the instant invention.

By "alkylaryl" is meant an aryl group substituted by one or more alkyl groups, wherein the "aryl" may be either a non-heteroaromatic ring system or heteroaromatic ring system.

By "addition salts" are meant salts of a given compound (or salt) of the invention derived from the chemical interaction with inorganic acids or organic acids. Acid addition salts may also be adducts with an organic solvent or water.

Examples of acid addition salts derived from inorganic acids include hydrochlorides, hydrobromides, hydroiodides, sulfates, hydrogensulfates, phosphates, monohydrogenphosphates, dihydrogenphosphates, nitrates, and thiocyanates. Examples of acid addition salts derived from organic acids include carboxylates, sulfonates, and phosphonates. Examples of acid addition salts derived from a carboxylic acid include formates, acetates, propionates, butyrates, cinnamates, benzoates, lactates, oxalates, malonates, succinates, glutarates, adipates, maleates, fumarates, phthalates, citrates, tartarates, salicylates, nicotinates, mandelates and salts from amino acids. Examples of acid addition salts derived from a sulfonic acid include alkylsulfonates (e.g. methanesulfonates, benzenesulfonates (e.g. p-toluenesulfonates), naphthlenesulfonates and camphorsulfonates. Examples of acid addition salts derived from a phosphonic acid include alkylphosphonates (e.g. methylphosphonates) and benzenephosphonates (e.g. phenylphosphonates).

"Substantially anhydrous conditions" is defined as conditions sufficient to conduct the diazotization or dediazotization without an undesirable decrease in the efficiency of the process while taking into account the costs and benefits of obtaining the appropriate reagents and reactor design. Preferably, the diazotization or dediazotization reactions are conducted in the absence of water.

The compounds of formula I are useful as intermediates for preparing pyridylsulfonylureas which are ultimately useful as herbicides and plant-growth regulators. For example, Schemes V and VI illustrate certain synthetic routes wherein 2-chloro-3-(2,2,2-trifluoroethoxy)pyridine is used as an intermediate for the production of a known pyridylsulfonylurea which is useful as an herbicide for controlling weeds in corn and sugar cane crops. See U.S. Pat. Nos. 5,403,814 and 5,579,583 which are hereby incorporated by reference. The individual transformations in Schemes V and VI may be accomplished by using means generally known to one of ordinary skill in the art. See for example U.S. Pat. Nos. 5,403,814 and 4,522,645, and EP-A-103543, which are hereby incorporated by reference.

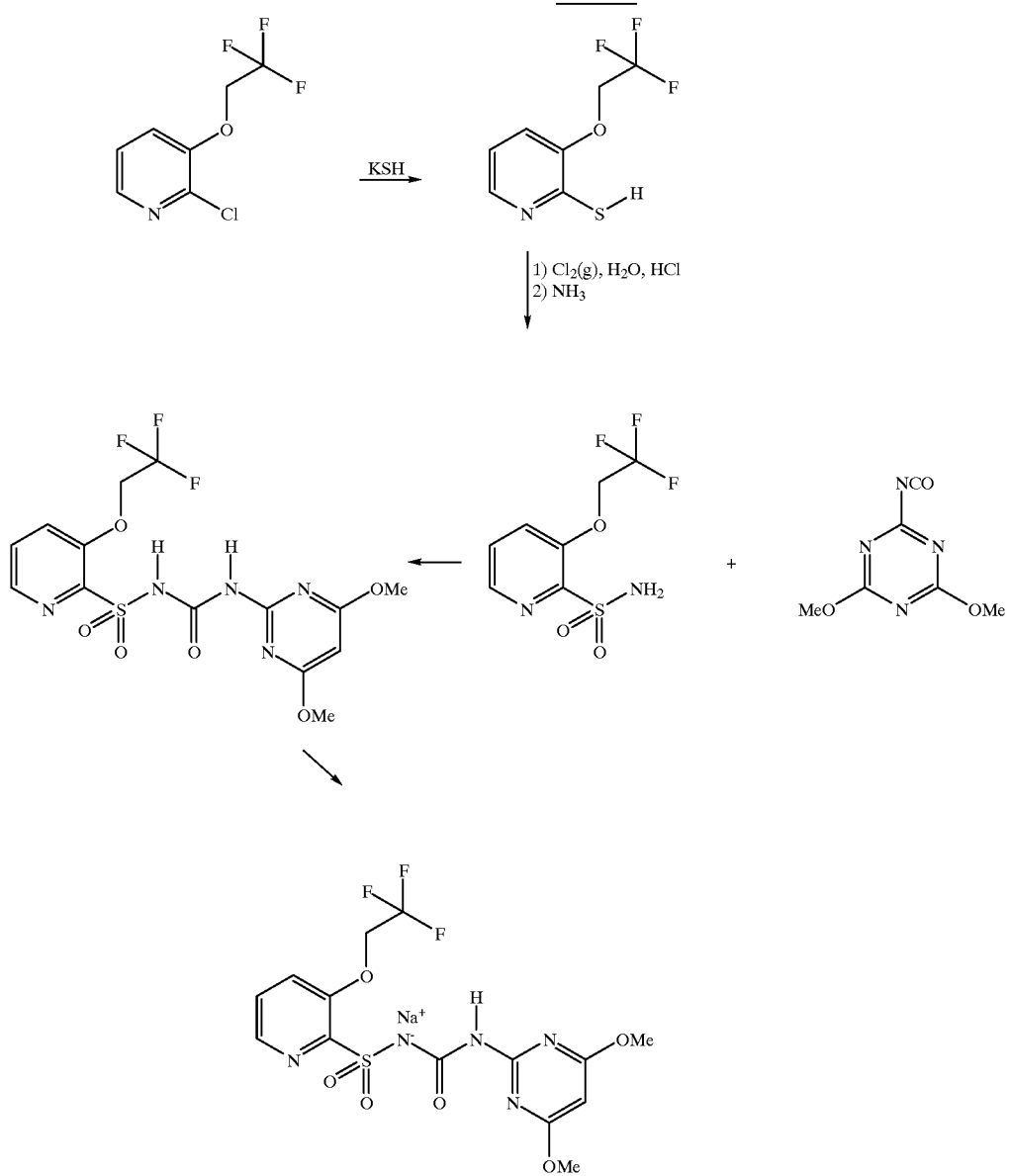
Scheme V
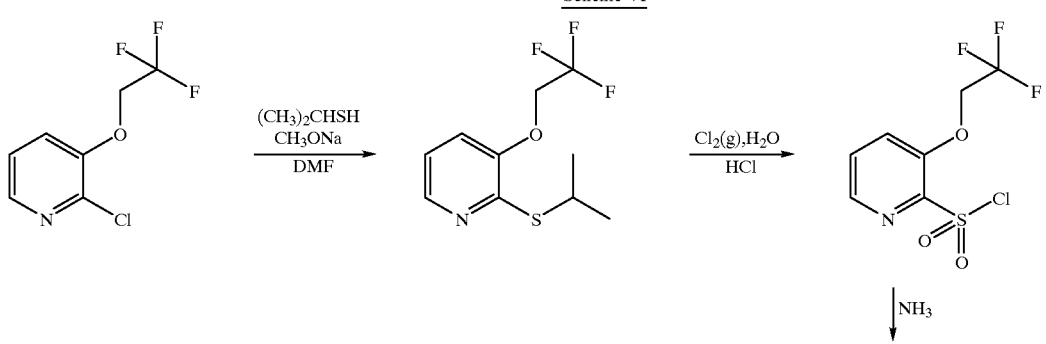
Scheme VI

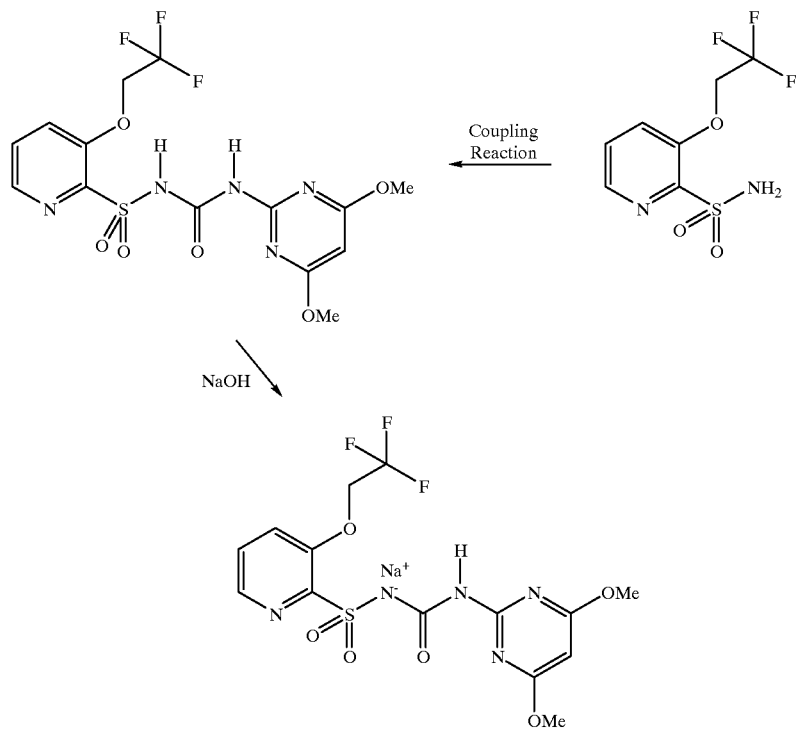

The compounds of formula I wherein $R_4$ is hydrogen can also be used to make the compounds of formula I wherein $R_4$ is a chloro or bromo. The synthetic transformation may be accomplished via an electrophilic aromatic substitution reaction. Typical chlorinating reagents that may be used are $FeCl_3$, $AlCl_3$, N-chlorosuccinimide or $SO_2Cl_2$. Typical brominating reagents that may be used are $FeBr_3$ and N-bromosuccinimide. The reactions preferably are run in the absence of light.

The following examples illustrate further some of the specific features of the invention but are not intended to limit its scope. Where not otherwise specified throughout this specification and claims, temperatures are given in degrees centigrade.

EXAMPLE 1

A reactor vessel is charged with 3-amino-2-chloropyridine (2.7 g, 21 mmol), 2,2,2-trifluoroethanol (15 g, 150 mmol), and trifluoroacetic acid (3.63 g, 31.8 mmol). The solution is cooled to 15° C. and magnesium sulfate (2.6 g) is charged to the vessel. The reagent t-butyl nitrite (2.51 g of a 96% solution, 23.4 mmol) is added drop-wise to the vessel while maintaining the temperature in the range 15° C. to 20° C. The solution is neutralized with aqueous saturated sodium bicarbonate solution and then extracted with MTBE. The solvent is removed by evaporation to obtain 2-chloro-3-(2,2,2-trifluoroethoxy)pyridine as a crude oil (1.58 g, crude yield 35.6%).

EXAMPLE 2

A reactor vessel is charged with 3-amino-2-chloropyridine (2.7 g, 21 mmol), 2,2,2-trifluoroethanol (15 g, 150 mmol), and trifluoroacetic acid (3.63 g, 31.8 mmol). The solution is cooled to the range 0° C. to 5° C. and then the reagent t-butyl nitrite (2.51 g of a 96% solution, 23.4 mmol) is added drop-wise to the vessel maintaining the temperature in the range 0° C. to 5° C. After stirring a few minutes the solution is transferred drop-wise to a reactor vessel containing 2,2,2-trifluoroethanol (20 g, 200 mmol) maintained at 55° C. The temperature rose to 70° C. during the drop-wise addition of the diazonium salt reaction mass. After cooling the solution, it neutralized with aqueous saturated sodium bicarbonate solution and then extracted with MTBE. The solvent is removed by evaporation to obtain 2-chloro-3-(2,2,2-trifluoroethoxy)pyridine as a crude oil (3.36 g) with an actual yield of 62.6%.

EXAMPLE 3

A reactor vessel is charged with 3-amino-2-chloropyridine (2.7 g, 21 mmol), 2,2,2-trifluoroethanol (15 g, 150 mmol), methanesulfonic acid (2.02 g, 21 mmol), and magnesium sulfate (3 g). The solution is cooled to the range 0° C. to 5° C. and then the reagent t-butyl nitrite (2.51 g of a 96% solution, 23.4 mmol) is added drop-wise to the vessel maintaining the temperature in the range 0° C. to 5° C. After stirring a few minutes the solution is transferred drop-wise to a reactor vessel containing 2,2,2-trifluoroethanol (20 g, 200 mmol) maintained at 65° C. to 70° C. After cooling the solution it is neutralized with aqueous saturated sodium bicarbonate solution and then extracted with MTBE. The solvent is removed by evaporation to obtain 2-chloro-3-(2,2,2-trifluoroethoxy)pyridine as a crude oil (4.4 g) with an actual yield of 70.1%.

EXAMPLE 4

A reactor vessel is charged with 3-amino-2-chloropyridine (10 g, 77.8 mmol), 2,2,2-trifluoroethanol (55.6 g, 556 mmol), and after cooling in an ice bath, methanesulfonic acid (7.48 g, 77.8 mmol) is added. The solution is cooled to the range −5° C. to 0° C. and then the reagent t-butyl nitrite (2.51 g of a 96% solution, 23.4 mmol) is added drop-wise to the vessel while maintaining the temperature in the range −5° C. to 0° C. After stirring a few minutes the solution is transferred by Masterflex® pump to a reactor vessel containing 2,2,2-trifluoroethanol (74.1 g, 741 mmol) maintained at 65° C. to 70° C. The pump line is cleared into the second reactor with 2,2,2-trifluoroethanol (5 g, 50 mmol) and mesitylene (10 g). An additional 20 g mesitylene was charged to the reactor vessel and a distillation column is attached to the reactor. Impure 2,2,2-trifluoroethanol (114 g, 90% recovery) is distilled out of the vessel. After cooling the solution it is neutralized with aqueous saturated sodium bicarbonate solution and then extracted with MTBE. The volatiles were removed by evaporation to obtain 2-chloro-3-(2,2,2-trifluoroethoxy) pyridine as a crude oil (44 g) with an actual yield of 73%.

EXAMPLE 5

A reactor vessel is charged with 3-amino-2-chloropyridine (5.4 g, 42 mmol), 2,2,2-trifluoroethanol (50 g, 500 mmol), and methanesulfonic acid (4.1 g, 43 mmol). The solution is heated to the range 55° C. to 60° C. and then t-butyl nitrite (5.3 g of a 90% solution, 46 mmol) is added drop-wise to the vessel while maintaining the temperature at 60° C. to 65° C. After nitrogen evolution ceases, the solution is cooled, neutralized with aqueous saturated sodium bicarbonate solution and then extracted with MTBE. The solvent is removed by evaporation to obtain 2-chloro-3-(2,2,2-trifluoroethoxy)pyridine as a crude oil (11.1 g) with an actual yield of 67.3%.

EXAMPLE 6

A reactor vessel is charged with 3-amino-2-isopropylthiopyridine (3.0 g, 18 mmol), 2,2,2-trifluoroethanol (21 g, 210 mmol), and methanesulfonic acid (1.7 g, 18 mmol). The solution is heated to the range 65° C. to 70° C. and then t-butylnitrite (2.2 g of a 90% solution, 19 mmol) is added drop-wise to the vessel while maintaining the temperature at 65° C. to 70° C. After nitrogen evolution ceases, the solution is cooled, neutralized with aqueous saturated sodium bicarbonate solution and then extracted with MTBE. The solvent is removed by evaporation to obtain 2-isopropyl-3-(2,2,2-trifluoroethoxy)pyridine as a crude oil (4.22 g, crude yield 94%).

EXAMPLE 7

A reactor vessel is charged with 3-amino-2-bromopyridine (2.0 g, 11.4 mmol), 2,2,2-trifluoroethanol (20 g, 200 mmol), and methanesulfonic acid (1.7 g, 18 mmol). The solution is heated to the range 65° C. to 70° C. and then t-butylnitrite (1.46 g of a 90% solution, 12.7 mmol) is added drop-wise to the vessel while maintaining the temperature at 55° C. to 70° C. After nitrogen evolution ceases, the solution is cooled, neutralized with aqueous saturated sodium bicarbonate solution and then extracted with MTBE. The solvent is removed by evaporation to obtain 2-bromo-3-(2,2,2-trifluoroethoxy)pyridine as a crude oil (2.85 g, crude yield of 96%).

EXAMPLE 8

A reactor vessel is charged with 3-aminopyridine (2.0 g, 21 mmol), 2,2,2-trifluoroethanol (15 g, 150 mmol), and trifluoroacetic acid (3.63 g, 31.8 mmol). The solution is cooled to 15° C. and then t-Butylnitrite (2.51 g of a 96% solution, 23.4 mmol) is added drop-wise to the vessel so that the temperature rises to the range 25° C.–30° C. Potassium carbonate (4.4 g) is added to the vessel and the reaction mass is stirred overnight followed by dilution with water and extraction with ethyl acetate. The solvent is evaporated to obtain 3-(2,2,2-trifluoroethoxy)pyridine as a crude oil (3.94 g, crude yield 59.5%) with an actual yield of 56.8%.

EXAMPLE 9

A reactor vessel is charged with 3-amino-2-chloropyridine (15.0 g, 117 mmol), 2,2,2-trifluoroethanol (21 g, 210 mmol), and methanesulfonic acid (11.2 g, 117 mmol). The solution is heated to the range 50° C. to 60° C. and then t-butylnitrite (14.7 g of a 90% solution, 128 mmol) is added drop-wise to the vessel while maintaining the temperature at 50° C. to 60° C. After nitrogen evolution ceases, the solution is cooled and ethylene glycol is charged to the reactor. The vessel is put under vacuum and the solvent and other volatiles are distilled off. The reaction mass is then neutralized with aqueous saturated sodium bicarbonate solution and extracted with MTBE. The solvent is removed to leave an oil which is stirred several hours with 10% aqueous NaOH (23 g) followed by extraction with MTBE. MTBE is removed under vacuum to obtain 2-chloro-3-(2,2,2-trifluoroethoxy)pyridine as a crude oil (16.83 g) with an actual yield of 65.8%. Analysis by GC indicates the purity of the 2-chloro-3-(2,2,2-trifluoroethoxy) pyridine to be 91.4%. Recovery of the 2,2,2-trifluoroethanol solvent is 88.9% by weight.

EXAMPLE 10

A reactor vessel is charged with 3-amino-2-chloropyridine (2.7 g, 21 mmol), 2,2,2-trichloroethanol (21 g, 210 mmol), and methanesulfonic acid (2.0 g, 21 mmol). The solution is heated to the range 61° C. to 70° C. and then t-butylnitrite (2.65 g of a 90% solution, 23 mmol) is added drop-wise to the vessel while maintaining the temperature at 60° C. to 70° C. After nitrogen evolution ceases, the solution is cooled, neutralized with aqueous saturated sodium bicarbonate solution and then extracted with MTBE. The solvent is removed by evaporation to leave an oil (28.6 g) Analysis by proton NMR and mass spectroscopy indicates the oil is impure 2-chloro-3-(2,2,2-trichloroethoxy)pyridine in 2,2,2-trichloroethanol.

The synthetic transformations described in the examples above were conducted under substantially anhydrous conditions. The alkyl nitrite reagents used in the examples are in the form of a solution of the corresponding alcohol; GC=gas chromatography; NMR=nuclear magnetic resonance; MTBE=methyl tertiary-butyl ether. In the above examples, the actual yield of product was determined using GC analysis and based on internal standards and response factors of standards of known purity. The actual yields recited are based on the theoretical quantity that the starting pyridine could give and represent the actual amount of the desired product formed. A crude product yield in the examples refers to the quantity of isolated material in comparison with the theoretical quantity that the starting pyridine could give. This is only the actual yield of product if the isolated material is 100% product, which is not the case for the un-purified products described in these procedures.

In summary, it is seen that this invention provides new herbicidal intermediates and processes for preparing the same. Variations may be made in proportions, procedures and materials without departing from the scope of the invention as defined by the following claims.

What is claimed is:

1. A compound of formula I:

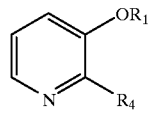
(I)

wherein $R_1$ is selected from the group consisting of —$CH_2CF_3$, —$CH_2CCl_3$, and —$CH_2CH_2Cl$; and $R_4$ is chloro.

2. A compound of claim 1 of formula:

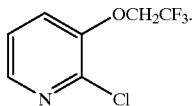

3. A process of preparing the compound of formula I:

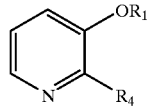
(I)

wherein $R_1$ is $C_1$–$C_4$ haloalkyl and $R_4$ is H, halogen or $C_1$–$C_4$ alkylthio; and acid addition salts thereof;

wherein the process comprises the step of reacting the diazonium salt of formula II:

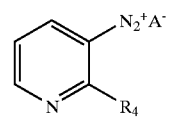
(II)

wherein $A^-$ is a counter-anion of the formula $^-OSO_2R_2$, wherein $R_2$ is $C_1$–$C_4$ alkyl, phenyl, $C_7$–$C_{10}$ alkylaryl or $C_5$–$C_{10}$ cycloalkyl, or $A^-$ is a counter-anion of the formula $^-OOC$—$R_{2a}$, wherein $R_{2a}$ is $C_1$–$C_4$ haloalkyl, with the alcohol having the formula of $R_1OH$, under substantially anhydrous conditions.

4. A process according to claim 3, wherein a stoichiometric excess amount of $R_1OH$ is used whereby the excess alcohol functions as the solvent for the reaction.

5. A process according to claim 3, wherein the diazonium salt has the formula:

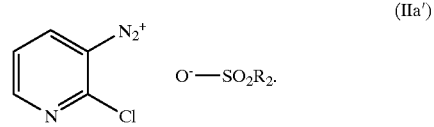
(IIa')

6. A process of claim 3 wherein $R_1$ is —$CH_2CF_3$ and $R_4$ is chloro.

7. A process of claim 3, where the diazonium salt of formula II is prepared by reacting 3-amino-2-chloropyridine with an alkyl nitrite and an acid in the presence of a solvent.

8. A process of claim 7, where the process is conducted without isolation of a diazonium salt intermediate.

9. A process of claim 7, wherein $R_1$ is —$CH_2CF_3$ and $R_4$ is chloro.

10. A process of claim 7, where the alkyl nitrite has the formula $R_3$—ONO, wherein $R_3$ is $C_1$–$C_5$ alkyl and the acid has the formula $R_2$—$SO_3H$ and the solvent has the formula $R_1OH$.

11. A process of claim 10, wherein the alkyl nitrite is t-butyl nitrite, the acid is methanesulfonic acid, and wherein the solvent and alcohol is 2,2,2-trifluoroethanol.

12. A product obtained by the process of reacting 3-amino-2-chloropyridine with an alkyl nitrite and an acid, in the presence of an alcohol of the formula $R_1OH$ wherein $R_1$ is selected from the group consisting of —$CH_2CF_3$, —$CH_2CCl_3$ and —$CH_2CH_2Cl$, under substantially anhydrous conditions.

* * * * *